(12) United States Patent
Isham (10) Patent No.: US 8,500,618 B2
(45) Date of Patent: Aug. 6, 2013

(54) DUAL GYNECOLOGICAL BALLOON PACKING SYSTEM

(75) Inventor: John Isham, Houston, TX (US)

(73) Assignee: RadiaDyne, LLC, Houston, TX (US)

(*) Notice: Subject to any disclaimer, the term of this patent is extended or adjusted under 35 U.S.C. 154(b) by 699 days.

(21) Appl. No.: 12/709,112

(22) Filed: Feb. 19, 2010

(65) Prior Publication Data
US 2010/0145132 A1 Jun. 10, 2010

Related U.S. Application Data

(63) Continuation-in-part of application No. 12/209,200, filed on Sep. 11, 2008, now abandoned.

(51) Int. Cl.
*A61N 5/00* (2006.01)
(52) U.S. Cl.
USPC .................................... 600/6; 600/3; 604/921
(58) Field of Classification Search
USPC ............... 600/1–8, 424, 427; 604/20, 21, 921
See application file for complete search history.

(56) References Cited

U.S. PATENT DOCUMENTS

| 4,430,076 | A | 2/1984 | Harris |
| 4,434,789 | A | 3/1984 | Kumar |
| 4,554,909 | A | 11/1985 | Pino y Torres |
| 5,012,357 | A | 4/1991 | Schoeppel et al. |
| 5,476,095 | A | 12/1995 | Schnall et al. |
| 5,562,594 | A | 10/1996 | Weeks |
| 5,653,683 | A * | 8/1997 | D'Andrea ................ 604/21 |
| 5,935,098 | A | 8/1999 | Blaisdell et al. |
| 5,947,891 | A | 9/1999 | Morrison |
| 6,312,375 | B1 * | 11/2001 | Montebello et al. ............ 600/6 |
| 6,390,968 | B1 | 5/2002 | Harmon |
| 6,641,518 | B2 | 11/2003 | Wolfson et al. |
| 6,699,171 | B2 | 3/2004 | Harmon et al. |
| 6,923,754 | B2 | 8/2005 | Lubock |
| 6,963,771 | B2 | 11/2005 | Scarantino et al. |
| 7,214,178 | B2 | 5/2007 | Lubock |
| 7,338,430 | B2 | 3/2008 | Lim et al. |
| 7,361,134 | B2 | 4/2008 | Rozenfeld et al. |
| 7,407,476 | B2 | 8/2008 | Lubock et al. |
| 7,465,268 | B2 | 12/2008 | Lubock et al. |

(Continued)

FOREIGN PATENT DOCUMENTS
WO WO2008148150 12/2008

OTHER PUBLICATIONS

D'Amico, Anthony V. et al., "A Practical Method to Achieve Prostate Gland Immobilization and Target Verification for Daily Treatment," Int. J. Radiation Oncology Biol. Phys., 2001 pp. 1431-1436. vol. 51 No. 5, © 2001 Elsevier Science Inc., U.S.A. (6 pages).

(Continued)

*Primary Examiner* — Charles A Marmor, II
*Assistant Examiner* — Carrie R Dorna
(74) *Attorney, Agent, or Firm* — Boulware & Valoir (57) ABSTRACT

A gynecological balloon apparatus has a first balloon and a second balloon disposed with a gynecological brachytherapy applicator. The first and second balloons are each movable between an inflated condition and a deflated condition. The first and second balloons may conform to a shape of a vaginal cavity when in their inflated conditions. A radiation detecting sensor and a motion detecting sensor may be positioned with the apparatus.

8 Claims, 5 Drawing Sheets

U.S. PATENT DOCUMENTS

| | | | |
|---|---|---|---|
| 7,556,596 B2 | | 7/2009 | Mourtada et al. |
| 7,771,340 B2 * | | 8/2010 | Axelrod et al. .................. 600/3 |
| 2003/0028097 A1 | | 2/2003 | D'Amico et al. |
| 2004/0015075 A1 * | | 1/2004 | Kimchy et al. .............. 600/424 |
| 2005/0240074 A1 | | 10/2005 | Lubock |
| 2006/0094923 A1 | | 5/2006 | Mate |
| 2006/0235260 A1 | | 10/2006 | Mourtada et al. |
| 2007/0078386 A1 | | 4/2007 | Salazar |
| 2009/0236510 A1 | | 9/2009 | Lacroix et al. |

OTHER PUBLICATIONS

Raghukumar, P. et al., "Design and Development of an Inflatable Latex Balloon to Reduce Rectal and Bladder Doses for Patients Undergoing High Dose Rate Brachytherapy." J. Med. Phys., 2009, pp. 48-51, vol. 34, No. 1, © 2009 Journal of Medical Physics (8 pages).

* cited by examiner

DUAL GYNECOLOGICAL BALLOON PACKING SYSTEM

CROSS-REFERENCE TO RELATED APPLICATIONS

This application is a continuation-in-part of co-pending U.S. application Ser. No. 12/209,200 filed on Sep. 11, 2008, which is hereby incorporated by reference for all purposes in its entirety.

STATEMENT REGARDING FEDERALLY SPONSORED RESEARCH OR DEVELOPMENT

N/A

REFERENCE TO MICROFICHE APPENDIX

N/A

BACKGROUND OF THE INVENTION

1. Field of the Invention

The present invention relates to gynecological balloons.

2. Description of the Related Art

Endometrial carcinoma, a malignant adenocarcinoma of the glandular epithelium lining the inner wall of the uterus, is one of the most common and serious disorders affecting the endometrium of post-menopausal women. Endometrial carcinomas represent an increasingly frequent tumor occurrence in industrialized countries. For example, in 1997, an estimated 170,000 new cases of endometrial carcinoma were diagnosed worldwide. The high occurrence of this malignancy necessitates the development of new therapeutic treatment alternatives. Moreover, early eradication of the carcinoma generally results in a more favorable prognosis for the patient. While surgical removal of the tumor is a preferred method of treatment, there may be some situations when a patient is unable to tolerate surgery. In some situations, a physician may prescribe one or more courses of preoperative radiation therapy. In yet further situations, surgery may be contraindicated or, particularly in the case of early stage carcinoma, even unnecessary. Additionally, it may be advisable for a patient who has undergone surgery to remove the tumor to undergo one or more courses of radiation therapy to eradicate any remaining tumor cells that may not have been excised.

Radiation therapy is used extensively to treat endometrial malignancies, either pre-operatively, as adjuvant therapy after surgery for patients with greater than stage IA disease, as primary therapy for patients unable to tolerate surgery, or to treat recurrences following surgery. Radiation therapy has been used for uterine cancers for over a century, and may be administered as either external beam treatment, brachytherapy, or both. In some cases, curative intracavitary brachytherapy may represent the most desirable treatment option. Curative intracavitary brachytherapy is frequently used to treat malignancies of the vagina, cervix, and endometrium (the lining of the uterus or vagina). Treatment of the endometrium by intracavitary brachytherapy may be referred to herein as intrauterine brachytherapy. While early stage tumors are more responsive to intracavitary implants, more extensive tumors may require treatment with interstitial implants and may involve a combination of external beam radiation therapy and intracavitary and/or interstitial brachytherapy.

Brachytherapy may also be described according to the length of time that a procedure is performed. Low dose rate (LDR) treatments typically require several days if the radioactive sources are temporarily placed in tissue. In some cases, permanent or semi-permanent implants may be preferred, wherein the materials remain in the tissue for a substantial portion of time. During most LDR brachytherapy procedures, a dose of radiation in the range of about 0.4-0.8 Gy/hr is administered. High dose rate (HDR) brachytherapy typically uses high specific activity gamma-emitting radionuclides to deliver a much greater dose (usually >0.4 Gy/min) of radiation to the site than what is administered using LDR brachytherapy. As such, HDR brachytherapy procedures are shorter in duration, and usually last less than an hour. HDR brachytherapy allows precise delivery of the radiation dose prescribed by the physician. The short treatment times, the amenability to performing HDR procedures on an outpatient basis, and accurate radiation delivery and improved patient comfort and compliance are all advantages of HDR brachytherapy.

A common gynecological applicator used for brachytherapy is often referred to as a tandem and ovoid set. The applicator usually comprises a curved tandem and a set of ovoids, each of which are at the end of control arms. The Utrecht Interstitial Fletcher Applicator supplied by Nucletron BV of The Netherlands is a tandem and ovoid set. Various patents have issued that concern advances in the typical cervical applicator. For example, U.S. Pat. No. 4,434,789, issued on Mar. 6, 1984 to Kumar, describes an apparatus for treating carcinoma of the uterine cervix by judiciously applying radioactive material immediately adjacent the uterine cervix for an extended period of time empirically determined by the radiologist. The applicator has three radioactively chargeable components including a central tubular tandem vaginally insertable into the cervix and two non-lineal tubular ovoids locatable at the cervix and positioned laterally between the respective vaginal walls and the uterine cervix. The ovoidal assemblies are removably and pivotably connected to the central tandem component.

Another common gynecological applicator used for brachytherapy is often referred to as a tandem and ring set. The applicator usually comprises a curved tandem and an interstitial ring, each of which are at the end of control arms. The Interstitial Ring Applicator supplied by Nucletron BV of The Netherlands is a tandem and ring set. A tandem and ring applicator has two radioactively chargeable components including a central tubular tandem vaginally insertable into the cervix and an interstitial ring locatable at the cervix and positioned laterally between the respective vaginal walls and the uterine cervix.

During the use of radiation therapy, it is important to direct the radiation dose to the targeted area while minimizing radiation received by other areas, such as the rectum and bladder. In the present situation, it is important to minimize the dosage received by the bladder and the rectal wall. Various patents and patent publications use shields to prevent complications due to misapplied radiation. U.S. Pat. No. 7,556,596, issued on Jul. 7, 2009 to Mourtada et al., proposes an adaptive brachytherapy applicator with remotely-controlled radial and longitudinal motion radioactive source lumen shields that can be manipulated by the radiation oncologist to optimize the dose distribution to the target and normal tissue structures for brachytherapy procedures.

U.S. Pat. No. 5,012,357, issued on Apr. 30, 1991 to Schoeppel et al., proposes a system with an applicator arrangement which has a pair of colpostats in conjunction with a tandem. The colpostats and tandem are formed of a material which is transparent to an imaging modality, such as CT scanning. Imaging-transparent source carriers containing dummy, or test, sources are placed in the colpostats. After the location of the colpostats, for example, has been determined, by imaging, the dummy source carriers are removed therefrom and replaced with selected source carriers containing actual radiation sources. The radiation source carriers further contain shielding which controls the strength and radiation pattern of the emitted radiation, all of which may be selected in response to the image. The dummy source carriers are provided with markings thereon, which are opaque to imaging, so that the position and orientation of the source carriers with respect to the tissue region to be irradiated can be determined from the images.

U.S. Pat. No. 5,947,891, issued on Sep. 7, 1999 to Morrison, proposes an instrument for treating vaginal malignancies which a tubular applicator, a separable vaginal retainer and an interlocking structure between the two. The tandem is adapted to receive a linear tube containing multiple sources of radiant energy and terminates at its inner end in a curved intrauterine portion. Two halves of the separable retainer surround the tandem and cooperatively form a vaginal cylinder for occupying the vaginal vault and a handle. The interlocking structure includes outwardly extending projections and cavities in the handle so positioned that the structure is visible to the physician at all times.

As discussed above, a very important consideration when treating patients using radiation therapy is that the proper dose of radiation reaches the treatment site. This is important whether the treatment method utilizes implanted radiation seeds, HDR, or external beams of radiation. Excessive dosing of the patient can lead to severe side effects including urinary incontinence and rectal bleeding issues. A proper treatment plan should deliver an adequate amount of radiation to the treatment site while minimizing the dose delivered to the surrounding tissues or organs at risk.

U.S. Pat. No. 6,963,771, issued on Nov. 8, 2005 to Scarantino et al., proposes a method, system and implantable device for radiation dose verification. The method includes (a) placing at least one wireless implantable sensor in a first subject at a target location; (b) administering a first dose of radiation therapy into the first subject; (c) obtaining radiation data from the at least one wireless implantable sensor; and (d) calculating a radiation dose amount received by the first subject at the target location based on the radiation data obtained from the at least one wireless sensor during and/or after exposure to the first administered dose of radiation to determine and/or verify a dose amount of radiation delivered to the target location.

U.S. Pat. No. 7,361,134, issued on Apr. 22, 2008 to Rozenfeld et al., proposes a method of determining the dose rate of a radiation source including locating three or more detectors in the vicinity of a source. Each of the detectors provides an output indicative of the amount of radiation received from the source and determines the location of the source from at least some of the detector outputs. International Pub. No. WO 2008/148150, published on Dec. 11, 2008 to Rozenfeld, proposes a semiconductor radiation sensor.

U.S. Patent Publication No. 2009/0236510, published on Sep. 24, 2009 to Lacroix et al., proposes a radiation dosimeter for measuring a relative dose of a predetermined radiation type within a detection region by using a plurality of scintillating optical fibers. U.S. Patent Publication No. 2006/0094923, published on May 4, 2006 to Mate, proposes a marker comprising a wireless transponder configured to wirelessly transmit a location signal in response to a wirelessly transmitted excitation energy.

During use of a traditional applicator, a treating professional must secure the device within the vaginal cavity. This is usually done by packing the cavity with gauze strips, which can be both time consuming, unreliable, and uncomfortable to the patient even to the point anesthesia may be administered. Various patents have issued which attempt to avoid this step and improve the process. For example, U.S. Pat. No. 4,554,909, issued on Nov. 26, 1985 to Pino y Torres, proposes a therapeutic instrument and method for radiation treatment of patients with carcinoma of the cervix and uterus. An elongated uterovaginal tandem having a curved proximal end is inserted in the uterine cavity, and an intravaginal applicator having a bore receiving the tandem is slid over the tandem into the vagina, and the tandem and applicator are fixed so that no relative motion therebetween is possible. The applicator obviates the need for packing of the vagina, having a quadrate cross-section, with rounded corners that substantially fills the vagina if the appropriate size of applicator is selected. Sutures are used to connect the distal end of the applicator adjacent the vaginal introitus. The applicator is then loaded with a pair of containers of irradiative material. The containers are inserted utilizing handles through passageways in the applicator to cavities in the applicator on either side of the tandem and adjacent the slanted proximal end of the applicator. The tandem is located with respect to the applicator cavities so that a greater distance is provided between the irradiative material containers and the vaginorectal septum.

The above discussed U.S. Pat. Nos. 4,434,789; 4,554,909; 5,012,357; 5,947,891; 6,963,771; 7,361,134; and 7,556,596; and Pub. Nos. U.S. 2006/0094923 and 2009/0236510; and International Pub No. WO 2008/148150 are hereby incorporated by reference for all purposes in their entirety.

A need exists for a gynecological apparatus to immobilize and displace the region surrounding the vaginal cavity during pre-treatment simulation and target localization, as well as during the delivery of radiation therapy to treat gynecological malignancy.

BRIEF SUMMARY OF THE INVENTION

A first and second balloon may be disposed with a gynecological brachytherapy applicator. In one embodiment, the gynecological brachytherapy applicator may have a tandem affixed to the end of a tandem control arm, a first ovoid affixed to the end of a first ovoid control arm, and a second ovoid affixed to the end of a second ovoid control arm. In another embodiment, the gynecological brachytherapy applicator may have a tandem affixed to the end of a tandem control arm, and a ring affixed to the end of a ring control arm. In other embodiments, the gynecological brachytherapy applicators may have other configurations for LDR or HDR brachytherapy treatments.

A first balloon may be affixed over an end of a first shaft or lumen having a passageway extending therethrough communicating with an interior of the first balloon for moving the first balloon between deflated and inflated conditions. Similarly, a second balloon may be affixed over an end of a second shaft or lumen having a passageway extending therethrough communicating with an interior of the second balloon for moving the second balloon between deflated and inflated conditions. The first and second balloon shafts may be affixed adjacent the gynecological brachytherapy applicator using one or more attachment clips.

In one embodiment, the first and second balloons may be affixed adjacent to at least one of the tandem control arm, the first ovoid control arm, or the second ovoid control arm. In another embodiment, the first and second balloons may be affixed adjacent to at least one of the tandem control arm or the ring control arm. The first and second balloons may each have a thicker substantially flat film surface for positioning adjacent the gynecological brachytherapy applicator to allow a support structure for the balloons to displace off of the gynecological brachytherapy applicator, and a thinner displacement film surface not adjacent to the gynecological brachytherapy applicator.

In their inflated conditions, the first and second balloons may conform to the shape of a vaginal cavity. One or more fiducial markers may be positioned with the first balloon, the first balloon shaft, the second balloon, the second balloon shaft, or any combination of the above. The fiducial markers are of a radio-opaque material. The apparatus may have at least one motion detecting sensor that may detect the movement of one or more fiducial markers, the first balloon surface, the first balloon shaft, the second balloon surface, the second balloon shaft, the surrounding anatomy, or any combination of the above. The apparatus may also have at least one radiation detecting sensor positioned with the first balloon, the first balloon shaft, the second balloon, the second balloon shaft, or any combination of the above for sensing an amount of radiation received. The motion detecting sensor may detect the movement of the radiation detecting sensor.

BRIEF DESCRIPTION OF THE DRAWINGS

A better understanding of the present invention can be obtained with the following detailed descriptions of the various disclosed embodiments in the drawings.

DETAILED DESCRIPTION OF THE INVENTION

Figure 1:
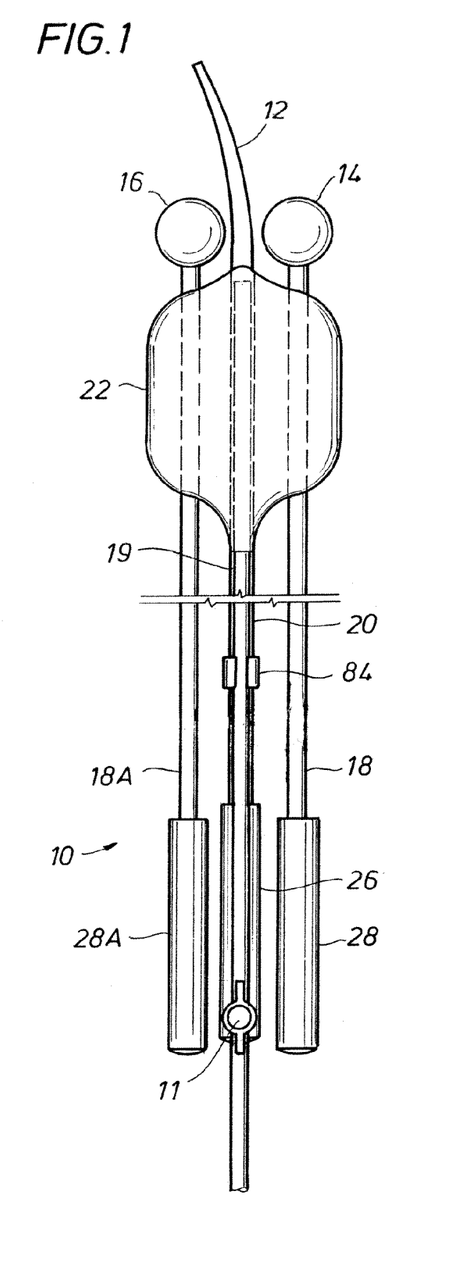
FIG. 1 is a plan top view of a gynecological applicator apparatus with a first balloon in the inflated position and a first balloon lumen disposed with a gynecological brachytherapy applicator having two ovoids and a tandem.

In FIG. 1, there is shown an embodiment of a cervix or gynecological balloon applicator apparatus 10. The gynecological applicator apparatus 10 includes a gynecological brachytherapy applicator comprising a curved tandem 12 formed at the end of a tandem control arm 20, first 14 and second 16 ovoids on each side of the tandem 12, which ovoids 14, 16 are attached to the ends of respective first 18 and second 18A ovoid control arms. Ovoid arms 18, 18A are attached to respective ovoid arm handles 28, 28A. It is also contemplated that a tandem 12 that is not curved may be used. A joint (not shown) may pivotally connect ovoid arms 18, 18A with each other and the tandem arm 20. Tandem arm handle 26 is attached with tandem arm 20.

Figure 2:
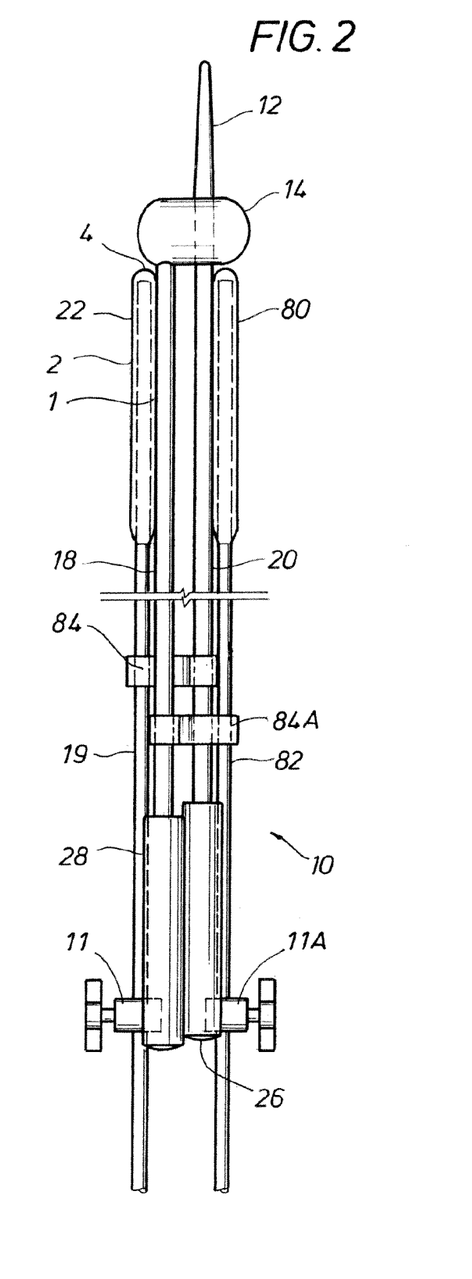
FIG. 2 is a side elevational view of the cervix applicator apparatus of FIG. 1 showing the first balloon and second balloon in their deflated conditions, and the first balloon lumen and second balloon lumen disposed with the gynecological brachytherapy applicator with attachment clips.
Figures 3, 3A:
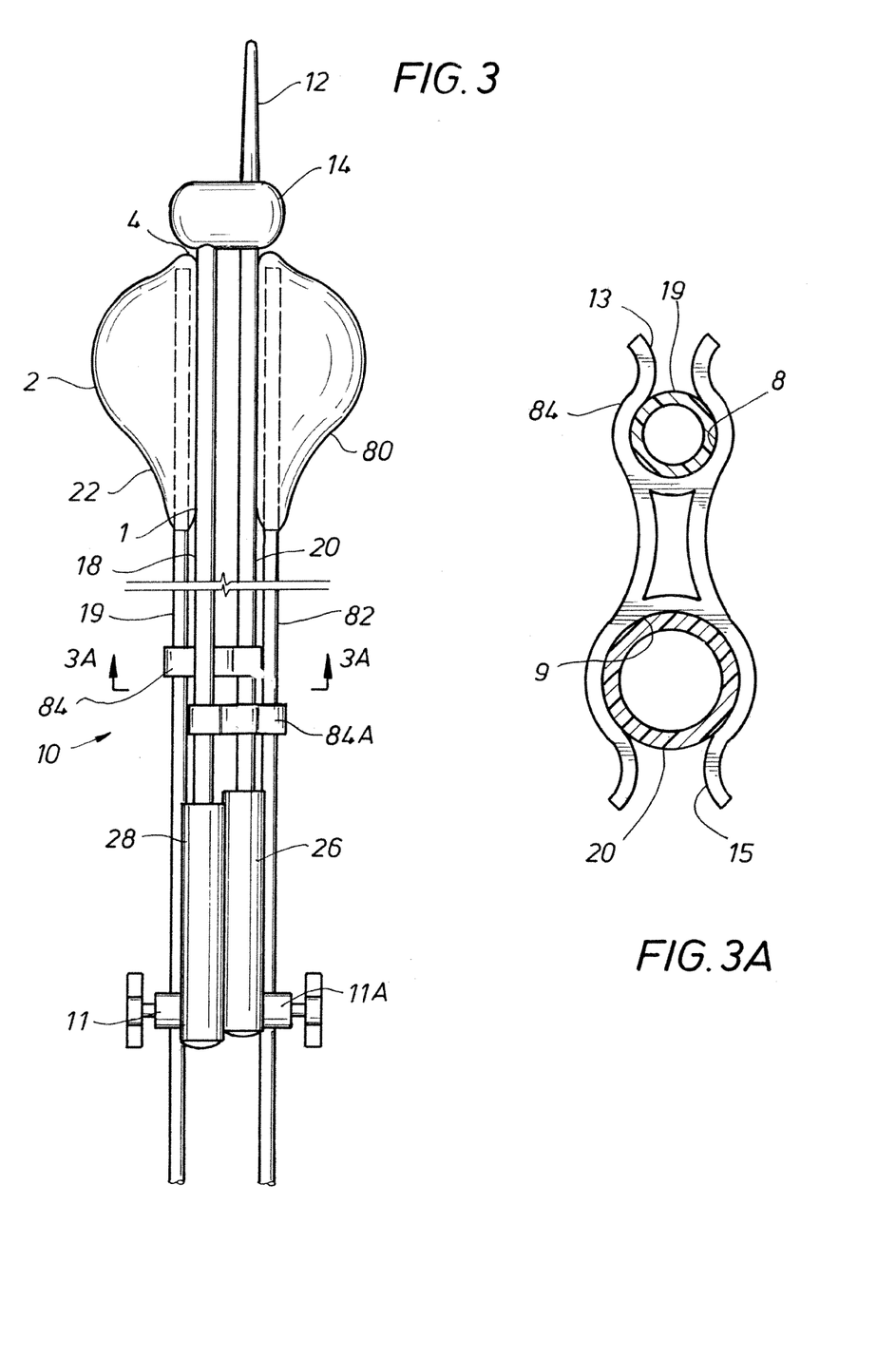
FIG. 3 is a side elevational view of the apparatus of FIG. 1 showing the first balloon and the second balloon in their inflated conditions.
FIG. 3A is a section view along line 3A-3A of FIG. 3 showing an attachment clip for positioning the first balloon shaft with the gynecological brachytherapy applicator.

At one end of the cervix applicator apparatus 10 adjacent tandem 12 and ovoids 14, 16 is a first balloon 22 shown in its inflated condition and attached with the first balloon shaft or lumen 19, which may extend longitudinally along the tandem arm 20. The first balloon shaft may be disposed with the tandem arm with attachment clip 84. A first balloon shaft valve 11 is disposed with first balloon shaft 19. A second balloon 80 and second balloon shaft or lumen 82 are not shown in this view as they are positioned below the first balloon 22 and first balloon lumen 19, but they are shown in FIGS. 2 and 3. However, other positions and orientations are contemplated. It is contemplated that the first balloon lumen 19 could extend along either the tandem control arm 20 or either of the ovoid arms 18, 18A. Likewise, the second balloon lumen 82 could extend along either the tandem arm 20 or either of the ovoid arms 18, 18A.

The first balloon lumen or shaft 19 is in communication with the interior of the first balloon 22, and is used to inflate and deflate the first balloon 22. The second balloon lumen 82 is in communication with the interior of the second balloon 80, and is used to inflate and deflate the second balloon 80. The first balloon 22 and second balloon 80 may also be filled with a radio-opaque and/or a radioactive fluid through their respective lumens 19, 82 should the circumstances require such a treatment. The first balloon 22 and the second balloon 80 for all embodiments shown in all of the Figures may be made of a non-latex material so as to avoid potential allergic reactions. Other materials are contemplated. The balloons 22, 80 may have the inflated shapes shown in FIGS. 3, 4, 5 and 8. Other shapes are contemplated.

FIG. 2 shows a side elevational view of the cervix applicator apparatus 10, with the first balloon 22 and the second balloon 80 in their uninflated or deflated conditions. In the uninflated condition, the first balloon 22 and the second balloon 80 may be in tight juxtaposition against the ovoid arms 18, 18A and the tandem arm 20. Such a position minimizes patient discomfort and makes insertion easier by treating professionals. In the uninflated condition, the first balloon 22 and the second balloon 80 may be in vacuumed states, making for a tighter juxtaposition against the ovoid arms 18, 18A and the tandem arm 20. Ovoid 14 is shown as having a cylindrical shape, but the ovoids 14, 16 may have a variety of shapes. The first balloon 22 and the second balloon 80 may be positioned on opposite sides of the ovoid arms 18, 18A and the tandem arm 20 with attachment clips 84, 84A, which are shown in detail view in FIG. 3A. In FIGS. 2 and 3, the first balloon shaft 19 is attached with the tandem arm 20 with clip 84, and the second balloon shaft 82 is attached with first ovoid arm 18 with clip 84A. However, it is contemplated that either first 19 or second 82 balloon shafts may be attached with tandem arm 20, either of ovoid arms 18, 18A, or with each other using one or more clips 84, 84A. It is also contemplated that no clips 84, 84A may be used. The flexibility of the balloon shafts 19, 82 allows them to be bent as necessary to position their respective balloons 22, 80. For example, even though the first 19 and second 82 balloon shafts are positioned with different arms 20, 18 in FIGS. 2 and 3, the second balloon shaft 82 may be manipulated so that the second balloon 80 is positioned below the first balloon 22 as shown in FIGS. 1-3.

Figure 8:
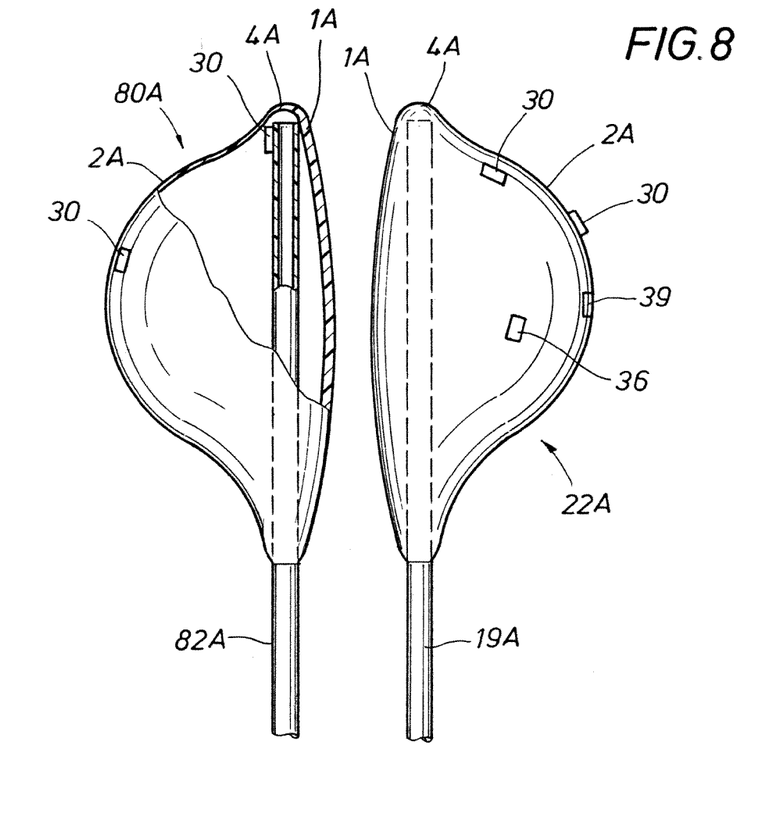
FIG. 8 is an isolated side elevational view of an opposing first balloon and second balloon in partial cut away section showing a radiation detecting sensor, a motion detecting sensor, and fiducial markers positioned with the first balloon, and fiducial markers positioned with the second balloon and second balloon shaft.

For all embodiments shown in all Figures, the balloons 22, 80 may each have a first portion, such as first portion 1 shown in FIGS. 2 and 3, and first portion 1A shown in FIG. 8, with a thicker substantially flat film surface for positioning adjacent the tandem control arm 20 and/or ovoid arms 18, 18A, and a second portion, such as second portion 2 shown in FIGS. 2 and 3, and second portion 2A shown in FIG. 8, with a thinner displacement film surface not adjacent to the tandem control arm 20 and/or ovoid arms 18, 18A. The substantially thicker and flat film surface of first portion 1, 1A may allow a support structure for the balloons 22, 22A, 80, 80A to displace off of the tandem control arm 20 and/or ovoid arms 18, 18A. Each of the balloons 22, 22A, 80, 80A may be made from two or more materials with different thicknesses attached together, such as by thermally welded bond at location 4 shown in FIGS. 2 and 3, and location 4A shown in FIG. 8. Other locations are contemplated. It is also contemplated that each of the balloons 22, 22A, 80, 80A may be made from two or more materials with substantially the same thicknesses but with different elasticity properties, such as different modulus of elasticity.

FIG. 3 shows the side elevational view of the cervix applicator apparatus 10, with the first balloon 22 and the second balloon 80 in their inflated conditions. As can be now understood, the first 22 and second 80 balloons may have substantially identical inflated shapes, but rotated 180° from each other about a longitudinal axis. Other shapes and configurations are contemplated. Second balloon shaft 82 is positioned with second balloon shaft valve 11A.

FIG. 3A shows attachment clip 84, which may be used to attach first balloon shaft 19 with tandem control arm 20. Clip has a first end 13 and a second end 15. The first end groove 8 inside diameter may be sized to fit the outside diameter of first balloon shaft 19. The second end groove 9 inside diameter may be sized to fit the outside diameter of tandem arm 20. First end groove 8 inside diameter may not be the same size as second end groove 9 inside diameter. Although first end groove 8 inside diameter appears smaller than second end groove 9 inside diameter, it is contemplated that first balloon shaft 19 may have a larger diameter than tandem control arm 20, so that first groove 8 inside diameter may be larger than second end groove 9 inside diameter. The clip 84 may also be sized to position the first balloon shaft 19 with first or second ovoid control arms 18, 18A. The clip 84 may be sized to position the first balloon shaft 19 with the second balloon shaft 80, in which case the first 8 and second 9 groove inside diameters may be the same. Clip 84A shown in FIGS. 2 and 3 is contemplated to be similar in size and shape to clip 84. The clip 84 may preferably be made of plastic. However, other materials are contemplated. It is contemplated that more than one attachment clip 84 may be used. Attachment clip 84 may be used with all embodiments shown in all of the Figures. The clip may be approximately one inch in height and approximately ⅜ inch in length. Other dimensions are contemplated. There are a variety of other methods for positioning the balloons 22, 80 with the arms 18, 18A, 20.

Figure 4:
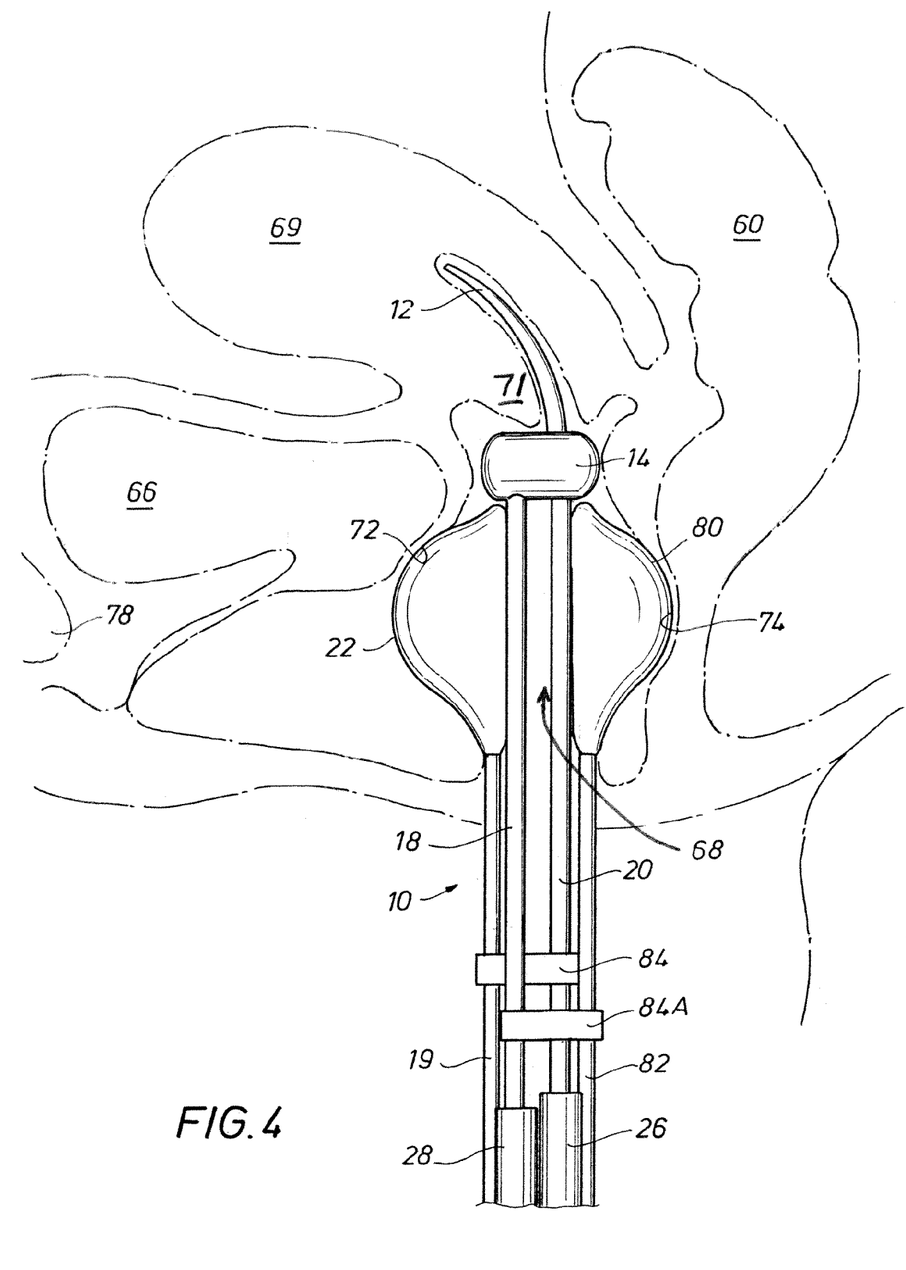
FIG. 4 is a side view of the gynecological applicator apparatus of FIGS. 1-3 within the vaginal cavity with the first balloon and the second balloons in their inflated conditions.

FIG. 4 shows a cross-sectional view of the cervix applicator apparatus 10 in a position for treatment within a patient's vaginal cavity 68. The curved tandem 12 is inserted into the patient's uterus 69. The ovoids 14, 16 generally rest up against the patient's cervix 71, within the vaginal cavity 68. Using a gynecological brachytherapy applicator, such as a tandem and ovoid set, the first balloon 22 and second balloon 80 secure the apparatus 10 in the desired position. When the apparatus 10 is positioned within the vaginal cavity 68, fluid or air or contrast may be introduced into the first balloon 22 through the first balloon lumen 19 and the second balloon 80 through the second balloon lumen 82 so as to inflate the balloons 22, 80.

The first balloon 22 and the second balloon 80 are shown in their inflated conditions. The first balloon 22 is inflated so as to rest up against and push against the anterior region 72 of the vaginal cavity 68. The first balloon 22 also pushes the bladder 66 away from the apparatus 10 and toward the pubic bone 78. The second balloon 80 rests up against and pushes against the posterior region 74 of the vaginal cavity 68. The second balloon 80 also pushes the rectum 60 away from the apparatus 10. By pushing both the rectum 60 and the bladder 66 away from the apparatus 10, the treatment is less likely to deliver doses of radiation to these organs at risk, which can cause complications. The first balloon lumen 19 and the second balloon lumen 82 are shown connected with clips 84, 84A and extending along the tandem arm 20 to a position outside the patient's body. It should be understood that the orientation of the apparatus 10 may be positioned differently than depicted in FIG. 4. For example, the apparatus may be rotated from its position in FIG. 4. It should also be understood that all embodiments shown in any of the Figures may be positioned as shown in FIG. 4.

Figure 5:
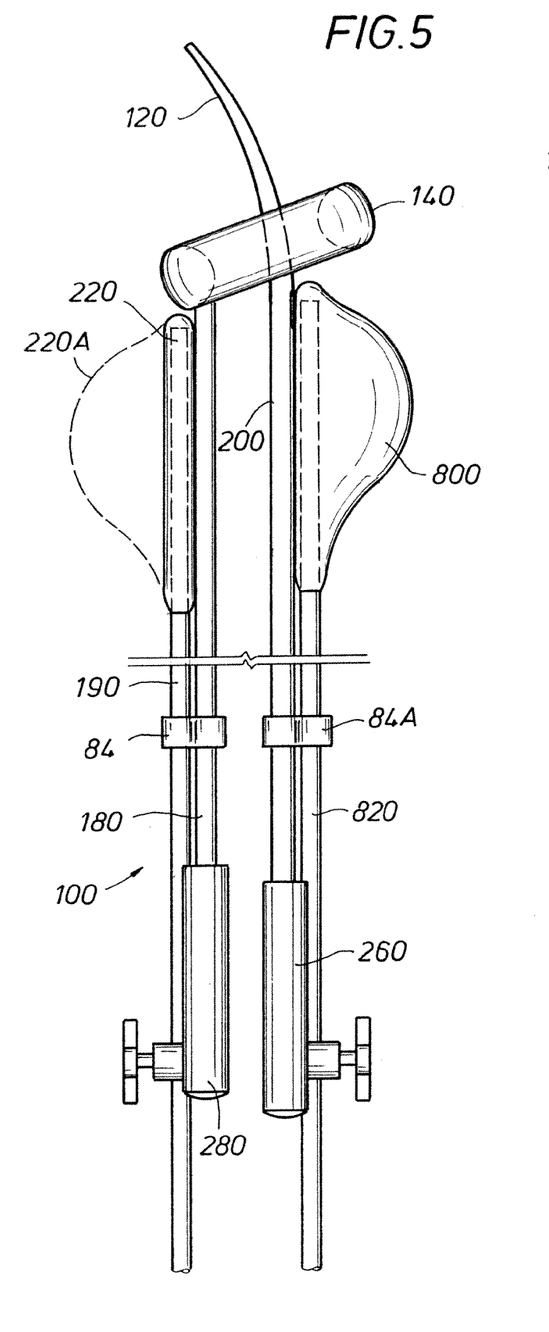
FIG. 5 is a side elevational view of a gynecological applicator apparatus with a first balloon in the deflated position and also shown schematically in the alternative inflated position, a second balloon in the inflated position, and a first balloon lumen and a second balloon lumen disposed with clips with a gynecological brachytherapy applicator having an interstitial ring and a tandem.

Turning to FIG. 5, there is shown another embodiment of a cervix or gynecological balloon applicator apparatus 100. The gynecological applicator apparatus 100 includes a gynecological brachytherapy applicator comprising a curved tandem 120 formed at the end of a tandem control arm 200, and an interstitial ring 140 attached to the end of ring control arm 180. It is also contemplated that a tandem that is not curved may be used. A joint (not shown) may pivotally connect ring arm 180 with the tandem arm 200. Ring control arm 180 is disposed with ring control arm handle 280 and tandem control arm 200 is disposed with tandem control arm handle 260.

At the end of the gynecological applicator apparatus 100 adjacent tandem 120 is a first balloon 220 shown in its deflated condition. It is contemplated that first balloon 220 may be inflated to its condition shown schematically at position 220A in FIG. 5. A second balloon 800 is shown in its inflated condition positioned below the gynecological applicator apparatus 100. For illustrative purposes the first balloon 220 is in its uninflated or deflated condition and the second balloon 800 in its inflated condition. In the deflated condition, the first balloon 220 and the second balloon 800 may be in tight juxtaposition against the ring arm 180 and the tandem arm 200. Such a position minimizes patient discomfort and makes insertion easier by treating professionals. In the uninflated condition, the first balloon 220 and the second balloon 800 may be in vacuumed states, making for a tighter juxtaposition against the ring arm 180 and the tandem arm 200.

The first balloon shaft 190 may be attached with the ring arm 180 with attachment clip 84. The first balloon shaft 190 may alternatively be attached with the tandem arm 200 using an attachment clip. It is also contemplated that there be no attachment clip used. The second balloon shaft 820 may be attached with the tandem arm 200 with attachment clip 84A. The second balloon shaft 820 may alternatively be attached with the ring arm 180 using an attachment clip. It is also contemplated that there be no attachment clip used. Other methods for positioning the balloons 220, 800 with the arms 180 and 200 are contemplated. The first 190 and second 820 balloon shafts may be positioned with each other. The first balloon 220 and the second balloon 800 may extend along the tandem arm 200 and ring arm 180. The first balloon lumen 190 and/or the second balloon lumen 820 could alternatively extend along the ring arm 180. The first balloon lumen 190 is in communication with the interior of the first balloon 220, and is used to inflate and deflate the first balloon 220. The second balloon lumen 820 is in communication with the interior of the second balloon 800, and is used to inflate and deflate the second balloon 800.

Figure 6:
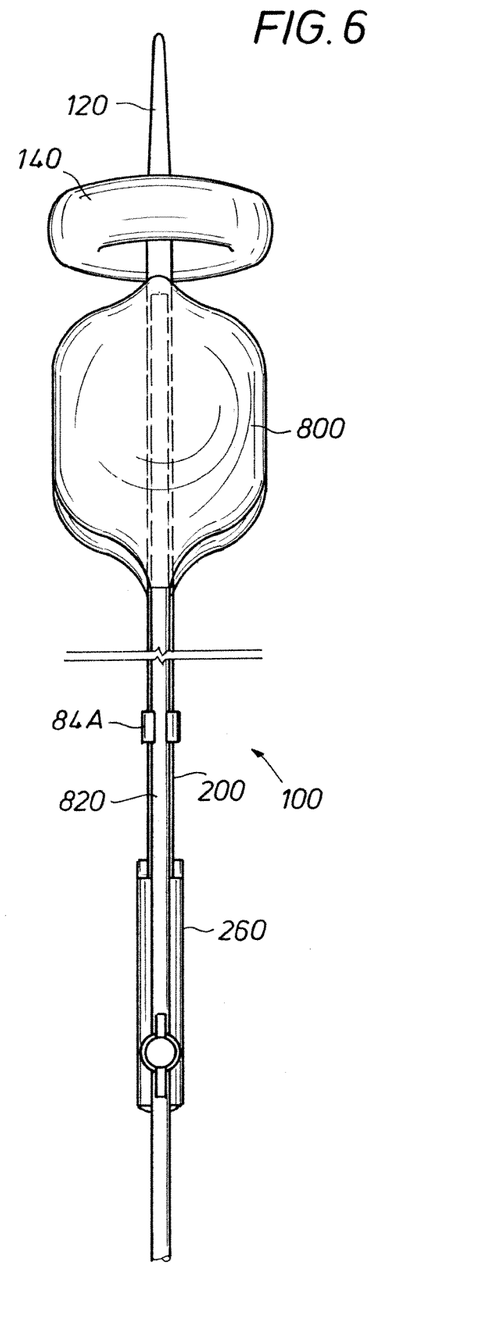
FIG. 6 is a plan bottom view of the cervix applicator apparatus of FIG. 5 showing the second balloon in its inflated condition, and the second balloon lumen disposed with the gynecological brachytherapy applicator.
Figure 7:
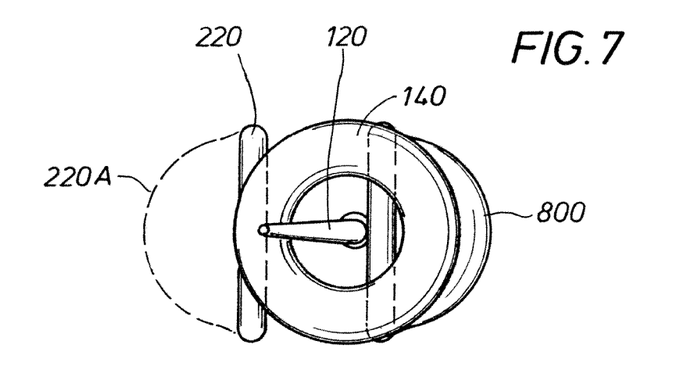
FIG. 7 is an elevational end view of the cervix applicator apparatus of FIG. 5 showing the interstitial ring, tandem, and first and second balloons.

While FIG. 5 shows the second balloon shaft 820 and second balloon 800 in side elevation view, FIG. 6 shows the second balloon 800 of FIG. 5 in plan bottom view, as seen rotated about a vertical axis 90° from FIG. 5. FIG. 7 shows the elevational end view of first 220 and second 800 balloons of FIG. 5. It is contemplated that other orientations of first 220 and second 800 balloons with applicator apparatus 100 may be used.

FIG. 8 shows an isolated view of a first balloon 22A and a second balloon 80A in their inflated positions as they may be with any gynecological applicator apparatus 10, 100 in any embodiment shown in any of the Figures. In this view, a plurality of fiducial markers 30 are shown positioned in an exemplary manner with the surfaces of the first 22A and second 80A balloons. A marker 30 is also shown on second balloon shaft or lumen 82A. It is also contemplated that one or more fiducial markers may be positioned with the first balloon shaft 19A and/or the second balloon shaft 82A. The fiducial markers 30 are a radio-opaque material, such as tungsten, in a film or solid marker. Other materials are contemplated. The fiducial markers 30 may be embedded in the materials used to form the balloons 22A, 80A, or attached or bonded to a surface of the balloons 22A, 80A, such as by epoxy. Other attachment means are contemplated. When the first 22A and second 80A balloons are is in their inflated conditions, the surfaces of the balloons 22A, 80A may reside against the surfaces of the vaginal cavity, such as shown in FIG. 4.

Using imaging techniques, the treating professional can view the location of the fiducial markers 30. By doing so, the treating professional can essentially view an image of the surface of the vaginal cavity, and ascertain the dose margins to the surrounding vaginal wall. The imaging enables the treating professional to more accurately place the cervix applicator apparatus 10, 100 in both treatment planning and successive treatments. A motion detecting device or sensor, such as sensor 39, may be positioned with the apparatus, such as with the first balloon 22A, the first balloon lumen 19A, the second balloon 80A, and/or the second balloon lumen 82A to determine the motion or movement of any or all of the fiducial markers 30 or the first 22A and/or second 80A balloon surfaces or the surrounding anatomy or any other part of the gynecological balloon apparatus, such as the gynecological brachytherapy applicator. The motion detecting sensor 39 may also be used to detect the movement of a radiation detecting sensor, such as sensor 36. More than one motion detecting sensor is also contemplated. The motion detecting sensor 39 may be selected from any of the available sensors that enable the user to detect motion. An electromagnetic type sensor is contemplated, although other types of motion detecting sensors are contemplated as well.

Also shown in FIG. 8 is radiation detecting sensor 36. Radiation sensor 36 is affixed to a surface of the first balloon 22A. Other locations are contemplated, such as first balloon shaft 19A, second balloon shaft 82A, and/or a surface of second balloon 80A. More than one radiation sensor is also contemplated. The radiation sensor 36 allows the treating professional to monitor the amount of radiation received at a particular site as well as plan their radiation delivery. International Pub No. WO 2008/148150 proposes a semiconductor radiation sensor that is contemplated. U.S. Pat. No. 7,361, 134 also proposes a type of radiation sensor that is contemplated. It is also contemplated that a radiation sensor using scintillating fiber optics may be used. A scintillating dosimetry radiation sensor may be used. A CPU and/or transponder may be used with software to electrically or wirelessly communicate with and interpret the information from the sensor(s).

As shown in the cut away section view of second balloon 80A, the thickness of the film material in first portion 1A may be different than the thickness of the film material in the second portion 2A. As previously discussed above, the thickness of the first portion 1A may be greater than the thickness of the second portion 2A to allow the first portion 1A to provide a platform for the balloon 22A, 80A to displace off of the gynecological brachytherapy applicator. First portion 1A and second portion 2A may be attached together at a location, such as location 4A.

For all embodiments shown in any of the Figures, sensors and markers positioned with first balloon 22, 22A, 220 may be positioned with second balloon 80, 80A, 800 and sensors and markers positioned with second balloon 80, 80A, 800 may be positioned with first balloon 22, 22A, 220. Similarly, sensors and markers positioned with first balloon lumen 19, 19A, 190 may be positioned with second balloon lumen 82, 82A, 820 and sensors and markers positioned with second balloon lumen 82, 82A, 820 may be positioned with first balloon lumen 19, 19A, 190. For all embodiments in all the Figures, first 22, 22A, 220 and second 80, 80A, 800 balloons are interchangeable, first 19,19A, 190 and second 82,82A, 820 balloon lumens are interchangeable, and first 22, 22A, 220 and second 80, 80A, 800 balloons may be interchangeably oriented within a vaginal cavity.

The foregoing disclosure and description of the invention are illustrative and explanatory thereof, and various changes in the details of the illustrated apparatus and system, and the construction and method of operation may be made without departing from the spirit of the invention.

I claim:

1. A vaginal balloon apparatus for use with a separate brachytherapy applicator, comprising:

first and second balloons, each balloon comprising a first material welded to a second material to form said balloon, said first material being thicker or less elastic than said second material;

each balloon further comprising a lumen with a single passageway in fluid communication with said balloon and a valve on said lumen for introducing a fluid into said balloon through said single passageway;

each lumen further comprising an attachment clip having a first end groove sized to fit an outside diameter of said lumen, and a second end groove sized to fit either an outside diameter of a separate brachytherapy applicator or the outside diameter of the other lumen, said first and second balloons being movable between a deflated condition and an inflated condition, wherein in said inflated condition said first material forms a flatter surface than said second material, and said second material conforms to the shape of a vaginal cavity.

2. The apparatus of claim 1, further comprising a fiducial marker with at least one of said balloons or lumens.

3. The apparatus of claim 2, said fiducial marker being a radio-opaque material.

4. The apparatus of claim 1, further comprising a motion detecting sensor positioned with a surface of said first balloon.

5. The apparatus of claim 1, further comprising a radiation detecting sensor positioned with a surface of said first balloon.

6. The apparatus of claim 5, said radiation detecting sensor being a semiconductor type sensor.

7. The apparatus of claim 5, said radiation detecting sensor being a scintillating fiber optics type sensor.

8. A method of gynecological brachytherapy, comprising attaching the first and second balloons of any of claims 1-7 to a separate brachytherapy applicator via said attachment clips, inserting said brachytherapy applicator and said first and second balloons into a patient, inflating said first and second balloons and treating said patient with brachytherapy.

* * * * *